| United States Patent [19] | [11] | 4,159,269 |
|---|---|---|
| Miller | [45] | Jun. 26, 1979 |

[54] PREPARATION OF OXAZOLIDINEDIONE DERIVATIVES OF VINCA ALKALOIDS

[75] Inventor: Jean C. Miller, Indianapolis, Ind.

[73] Assignee: Eli Lilly and Company, Indianapolis, Ind.

[21] Appl. No.: 883,112

[22] Filed: Mar. 3, 1978

[51] Int. Cl.$^2$ ............................................. C07D 519/04
[52] U.S. Cl. .................................. 260/244.4; 546/51; 260/307 B
[58] Field of Search ............. 260/287 B, 307 B, 244.4; 546/41, 51

[56] References Cited

U.S. PATENT DOCUMENTS 3,311,655  3/1967  Boileau et al. ................... 260/307 B

OTHER PUBLICATIONS

Morrison et al., Organic Chemistry, (1966), p. 927.

*Primary Examiner*—Donald G. Daus
*Assistant Examiner*—David E. Wheeler
*Attorney, Agent, or Firm*—James L. Rowe; Arthur R. Whale

[57] ABSTRACT

3-Spiro-5''-oxazolidine-2'',4''-dione derivatives of Vinca alkaloids, useful as anti-tumor agents, synthesized from a C-3 carboxamide and a dialkyl carbonate.

3 Claims, No Drawings

PREPARATION OF OXAZOLIDINEDIONE DERIVATIVES OF VINCA ALKALOIDS

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leuroformine (Belgian Pat. No. 811,110); leurosidine (vinrosidine) and leurocristine (to be referred to hereafter as vincristine) (both in U.S. Pat. No. 3,205,220); deoxy VLB "A" and "B", *Tetrahedron Letters*, 783 (1958); 4-desacetoxyvinblastine (U.S. Pat. No. 3,954,773; 4-desacetoxy-3'-hydroxyvinblastine (U.S. Pat. No. 3,944,544); leurocolombine (U.S. Pat. No. 3,890,325) and vincadioline (U.S. Pat. No. 3,887,565). Two of these alkaloids, VLB and vincristine, are now marketed as drugs for the treatment of malignancies, particularly the leukemias and related diseases in humans. Of these marketed compounds, vincristine is a most active and useful agent in the treatment of leukemias but is also the least abundant of the anti-neoplastic alkaloids of *Vinca rosea*. The two marketed alkaloids are customarily administered by the i.v. route.

Chemical modification of the Vinca alkaloids has been rather limited. In the first place, the molecular structures involved are extremely complex, and chemical reactions which affect a specific functional group of the molecule without changing other groups are difficult to develop. Secondly, alkaloids lacking desirable chemotherapeutic properties have been recovered or produced from *Vinca rosea* fractions or alkaloids, and a determination of their structures has led to the conclusion that these compounds are closely related to the active alkaloids. Thus, anti-neoplastic activity seems to be limited to very specific structures, and the chances of obtaining more active drugs by modification of these structures would seem to be correspondingly slight. Among the successful modifications of physiologically-active alkaloids has been the preparation of dihydro VLB (U.S. Pat. No. 3,352,868) and the replacement of the acetyl group at C-4 (carbon no. 4 of the VLB ring system-see the numbered structure below) with higher alkanoyl group or with unrelated acyl groups. (See U.S. Pat. No. 3,392,173.) Several of these derivatives are capable of prolonging the life of mice inoculated with P1534 leukemia. One of the derivatives in which a chloracetyl group replaced the C-4 acetyl group of VLB was also a useful intermediate for the preparation of structurally modified VLB compounds in which an N,N-dialkylglycyl group replaced the C-4 acetyl group of VLB (See U.S. Pat. No. 3,387,001). C-3 carboxamide derivatives of VLB, vincristine, vincadioline etc. have also been prepared and found to be active anti-tumor agents. (Belgian Pat. No. 813,168) These compounds are extremely interesting because, for example, the 3-carboxamides of VLB are more active against Ridgeway osteogenic sarcoma and Gardner lymphosarcoma than is VLB itself from which they are derived. Certain of the amide derivatives actually approach the activity of vincristine against these tumors. One of these amides, 4-desacetyl VLB C-3 carboxamide or vindesine, is currently on clinical trial in humans and has been found active in certain leukemias. In humans, vindesine appears to have less neurotoxicity than does vincristine.

Another group of active structures are the 3-spiro-5''-oxazolidine-2'',4''-dione derivatives of dimeric indole-dihydroindole alkaloids described in the copending application of Miller and Gutowski, Ser. No. 747,575, filed Dec. 6, 1976. These oxazolidinedione derivatives have good oral activity against transplanted tumors in mice.

SUMMARY OF THE INVENTION

This invention provides a process for synthesizing compounds represented by Formula I below:

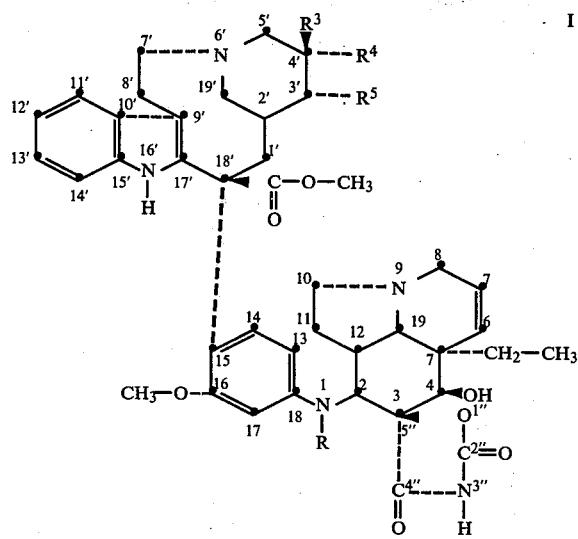

wherein R is $CH_3$ or CHO;
one of $R^3$ and $R^4$, when taken singly, is H or OH and the other $C_2H_5$;
$R^5$, when taken singly, is H;
and $R^4$ and $R^5$, when taken together, form an epoxide.

The process comprises reacting a C-3 carboxamide of the formula:

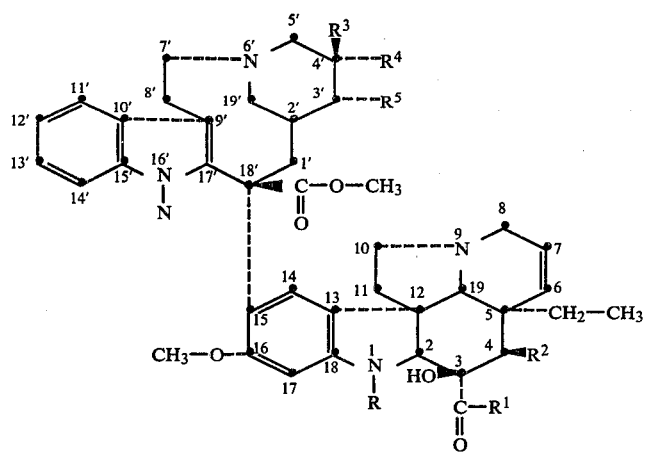

II wherein $R^1$ is $NH_2$, $R^2$ is OH or acetoxy; and R, $R^3$, $R^4$ and $R^5$ have the same meaning as before, with a lower alkyl carbonate $(R^6O)_2CO$, in which $R^6$ is methyl or ethyl, in the presence of at least two moles of sodium hydride or equivalent base in an inert solvent.

Compounds of formula I can be described generically as 4-desacetyl derivatives of VLB in which $R^1$ is acetoxy, R is methyl, $R^3$ is hydroxyl, $R^4$ is ethyl and $R^5$ is H, of vincristine in which $R^1$ is acetoxy, R is formyl, $R^3$ is hydroxyl, $R^4$ is ethyl and $R^5$ is H, of leurosidine in which $R^1$ is acetoxy, R is methyl, $R^3$ is ethyl, $R^4$ is hydroxyl and $R^5$ is H, of Deoxy VLB "A", in which $R^1$ is acetoxy, R is methyl, $R^3$ and $R^5$ are H and $R^4$ is ethyl; of Deoxy VLB "B" wherein R and $R^5$ are the same as in Deoxy VLB "A" but $R^3$ is ethyl and $R^4$ is hydrogen, or leurosine wherein $R^1$ is acetoxy, R is methyl, $R^3$ is ethyl and $R^4$ and $R^5$ taken together form an α-epoxide ring or of leuroformine, the corresponding compound in which R=CHO.

Each compound of this invention has been named as a 3-spiro-5″-oxazolidine-2″,4″-dione derivatives of the particular alkaloid listed above; for example, the oxazolidinedione derived from 4-desacetyl VLB would be named as 3-descarbomethoxy-3-deshydroxy-4-desacetyl VLB 3-spiro-5″-oxazolidine-2″,4″-dione. According to the above name, a spiro compound is formed in which the spiro carbon atom is carbon 3 of the vinca alkaloid ring system and carbon 5″ of the oxazolidinedione ring system. In naming the compounds of this invention systematically, the term "3-descarbomethoxy-3-deshydroxy" has been used to indicate that the carbomethoxy group and the hydroxy group at 3 have been replaced by (or incorporated into) the oxazolidine ring. In order to simplify the naming of the compounds of this invention, however, this term will be omitted hereafter since the presence of the oxazolidine ring in each of the compounds will be understood to have replaced the hydroxy and carbomethoxy groups at carbon 3 in the vinca alkaloid. It will be understood, therefore, that each name herein of an oxazolidinedione implicitly contains the terms "3-descarbomethoxy-3-deshydroxy".

The process of this invention involves first the reaction of a C-3 carboxamide derivative of a dimeric indoledihydroindole of Formula II wherein $R^1$ is $NH_2$ with an excess of sodium hydride or other suitable base in an inert solvent. The first mole of sodium hydride forms an anion with the amide group, and the second mole forms an anion with the C-3 hydroxyl. The C-4 acetoxy group is hydrolysed under the reaction conditions. Thus, the quantity of sodium hydride or other base used must be in excess of 2 moles per mole of C-3 carboxamide. In actual practice, a 10–20 fold excess is employed. The alkylcarbonate is then added and reacts with the dianion, though not necessarily simultaneously, to form the spirooxazolidinedione (formula I) with the formation of two moles of lower alkanol as a sodium or other metal salt. Among the inert solvents which can be used in the above reaction are included ethers such as THF, amides such as DMA or DMF and the like.

The spirooxazolidinedione product of the above reaction is isolated and purified by standard procedures.

The starting C-3 carboxamides (formula II where $R^1$ is $NH_2$) are prepared from the corresponding C-3 esters (formula II where $R^1$ is $OCH_3$) by procedures set forth in the copending application of Cullinan and Gerzon, Ser. No. 828,693 filed Aug. 29, 1977. These methods include reaction of compounds according to formula II in which $R^1$ is $OCH_3$ and the hydroxyl at C-4 is acylated, R, $R^3$, $R^4$, and $R^5$ having the same meaning as before, with hydrazine to form a compound according to Formula II in which $R^1$ is $NH-NH_2$ (the C-4 acetoxy group is hydrolyzed during this procedure). The hydrazide can then be hydrogenolized by Raney nickel to yield a C-3 carboxamide. Alternatively, the hydrazide group can be reacted with sodium nitrite to yield an azide. The azide can then be reacted with ammonia to form the C-3 carboxamide or it can be reduced with a metal hydride reducing agent to again form the C-3 carboxamide. Finally, the C-3 ester (formula II where $R^1$ is $OCH_3$) can be treated with ammonia in a sealed tube to yield the C-3 amide directly. This direct amidation reaction can provide a starting amide with C-4 acetoxyl intact since this ester group is not affected during the reaction. Useful starting materials include compounds in which C-4 can be either hydroxyl or acetoxyl, but the acetoxy is hydrolysed during the hydrazine procedure as set forth above.

The C-3 esters (Formula II where $R^1$ is methyl) from which the above C-3 amides are derived, can be isolated from the leaves of the plant *vinca rosea*. These C-3 esters include VLB, vincristine, leurosidine, leurosine, and deoxy VLB "A" and "B". Starting materials represented by formula II when R is formyl and $R^1$ is $OCH_3$ (except for vincristine which is obtained from leaves of *Vinca rosea*) are prepared as follows. The 1-methyl group of deoxy VLB "A" or "B", etc. (in fact, any compound represented by II in which R is methyl and $R^1$ is methoxy) can be oxidized with chromium oxide in glacial acetic acid at $-60°$ C. to yield a mixture of compounds in which R is H or formyl, according to the procedure set forth in U.S. Pat. No. 3,899,493. The compounds in which R is H can be reformylated to yield compounds in which R is CHO.

This invention is further illustrated by the following specific example.

EXAMPLE 1

PREPARATION OF 4-DESACETYL VLB 3-SPIRO-5"-OXAZOLIDINE-2",4"-DIONE

A suspension of 208.0 mg. of sodium hydride (as a 50% oil dispersion) was prepared in 20 ml. of tetrahydrofuran. 200.9 mg. of 4-acetyl vindesine (VLB C-3 carboxamide) were added thereto. After the solution had been stirred at ambient temperature for 25 minutes, 4.0 ml. of dimethylcarbonate were added. The reaction mixture was then stirred at ambient temperature for 4.5 hours after which time the volatile constituents were removed by evaporation. Water was added and the aqueous solution acidified with dilute hydrochloric acid. The acidic layer was extracted three times with methylene dichloride and the methylene dichloride extracts were discarded. The aqueous layer was then made basic with 10% percent aqueous sodium hydroxide. 4-Desacetyl VLB 3-spiro-5"-oxazolidine-2",4"-dione, being insoluble in the basic layer, separated and was extracted with 4 portions of methylene dichloride. The methylene dichloride extracts were combined and the solvent removed by evaporation. The residue weighing 98.4 mg. was subjected to preparative thin-layer chromatography over silica using a 1:1 ethyl acetate-methanol solvent system. 4 bands were seen, the fourth band comprising 4-desacetyl VLB 3-spiro-5"-oxazolidone-2",4"-dione. The band was separated mechanically and eluted from the silica. Evaporation of the eluting solvent yielded a residue weighing 10.9 mg. with the following physical characteristics. Nmr in deuterochloroform; δ at 0.90, 2.87, 3.57, 3.65, 3.84, 3.95, 5.5–6.0, 6.08, 8.5. Infrared spectrum, maxima at 3680, 3470, 1810, 1735, 1620, 1505, 1460, 1435, 1335, 1010, 910 cm$^{-1}$. Molecular spectrum; ions at 807, 793, 763, 749, 718, 706, 692, 690, 634, 434, 422, 408, 355, 351, 325, 323, 297, 295, 269, 268, 187, 167, 154, 149, and 135. Field desorption molecular ions; 779, 753, 735.

Higher yields of 4-desacetyl VLB 3-spiro-5"-oxazolidine-2",4"-dione are obtained (about 70 percent) if vindesine (4-desacetyl VLB 3-carboxamide) is used in place of 4-acetylvindesine in the above reaction.

Other carbonylating agents such as phosgene, carbonyldiimidazole, methylchloroformate, ethylchloroformate and the like can be used in place of dimethylcarbonate in the above reaction.

The oxazolidinedione prepared as above exists in tautomeric forms in which the hydrogen on the ring nitrogen can enolize with either of the carbonyl groups present in the ring to form an hydroxy oxazolinone. More specifically, the oxazolidine-2,4-dione can tautomerize to either a 2-hydroxy-2-oxazoline-4-one or a 4-hydroxy-3-oxazoline-2-one. It is believed that the product of the above reaction contains at least two of such tautomeric forms, if not all three.

3-Spiro-5"-oxazolidine-2",4"-diones of other dimeric indole-dihydro indole alkaloids according to Formula II when $R^1$ is $OCH_3$ are prepared by substituting for VLB C-3 carboxamide or 4-desacetyl VLB C-3 carboxamide in the above reaction 4-Desacetyl 4'-deoxy VLB "B" C-3 carboxamide,
4-Desacetyl 4'-deoxy VLB "A" C-3 carboxamide,
4'-Deoxy VLB "A" C-3 carboxamide,
4-Desacetyl leurosine C-3 carboxamide,
4-Desacetyl leuroformine C-3 carboxamide,
4-Desacetyl leurosidine C-3 carboxamide,
Leurosidine C-3 carboxamide,
4-Desacetylvincristine C-3 carboxamide or the like.

The products of such reaction are 3-spiro-5"-oxazolidine-2",4"-dione derivatives of 4-desacetyl Deoxy VLB "A" and "B", of leurosine and leuroformine and of leurosidine and vincristine.

The procedure of this invention constitutes a preferred method of preparing the 3-spiro-5"-oxazolidine-2",4"-diones of U.S. application Ser. No. 747,575 filed Dec. 6, 1978 in which the 3" nitrogen is unsubstituted.

Compounds preparable by the process of this invention are anti-tumor agents. For example, 4-desacetyl VLB 3-spiro-5"-oxazolidine-2",4"-dione gave 62–92 percent inhibition of growth of B16 melanoma in mice at dose levels of 0.2–0.8 mg/kg by the intraperitoneal route.

I claim:

1. The process which comprises the step of reacting a compound of the formula:

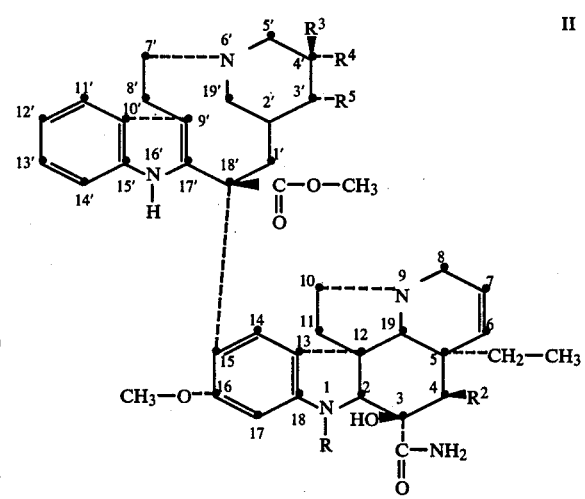

II wherein R is $CH_3$ or CHO; $R^2$ is OH or acetoxy;
one of $R^3$ and $R^4$, when taken singly, is H or OH and the other $C_2H_5$;
$R^5$, when taken singly, is H:
and $R^4$ and $R^5$, when taken together, form an epoxide;
with at least 2 moles of sodium hydride and at least one mole of an alkyl carbonate $(R^6O)_2CO$ wherein $R^6$ is methyl or ethyl in an inert solvent to yield a spirooxazolidinedione of the formula:

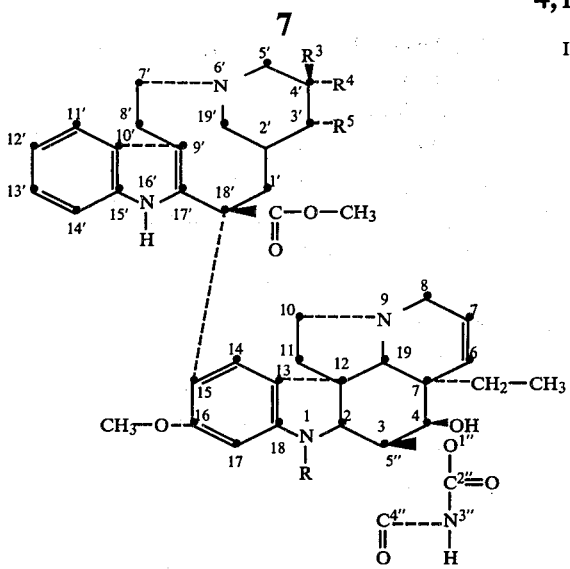

wherein R, $R^3$, $R^4$ and $R^5$ have the same meaning as hereinabove.

2. A process according to claim 1 in which VLB C-3 carboxamide is reacted with dimethyl carbonate to yield 4-desacetyl VLB 3-spiro-5''-oxazolidine-2'',4''-dione.

3. A process according to claim 1 in which 4-desacetyl VLB C-3 carboxamide is reacted with dimethylcarbonate to yield 4-desacetyl VLB 3-spiro-5''-oxazolidine-2'',4''-dione.

* * * * *